(12) United States Patent
Jacobsen et al.

(10) Patent No.: US 9,016,943 B2
(45) Date of Patent: *Apr. 28, 2015

(54) X-RAY MICROSCOPE SYSTEM WITH CRYOGENIC HANDLING SYSTEM AND METHOD

(71) Applicant: Carl Zeiss X-ray Microscopy, Inc., Pleasanton, CA (US)

(72) Inventors: Chris J. Jacobsen, Naperville, IL (US); Wenbing Yun, Walnut Creek, CA (US)

(73) Assignee: Carl Zeiss X-ray Microscopy, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/081,282

(22) Filed: Nov. 15, 2013

(65) Prior Publication Data

US 2014/0072104 A1    Mar. 13, 2014

Related U.S. Application Data

(63) Continuation of application No. 12/559,183, filed on Sep. 14, 2009, now Pat. No. 8,602,648.

(60) Provisional application No. 61/096,502, filed on Sep. 12, 2008.

(51) Int. Cl.
*G21K 7/00* (2006.01)
*G01N 23/04* (2006.01)

(52) U.S. Cl.
CPC .............. *G01N 23/04* (2013.01); *G01N 23/046* (2013.01); *G21K 7/00* (2013.01)

(58) Field of Classification Search
CPC ........ G21K 7/00; G01N 23/04; G01N 23/046

USPC .......................................... 378/43, 208, 4, 20
See application file for complete search history.

(56) References Cited

U.S. PATENT DOCUMENTS

| | | | |
|---|---|---|---|
| 4,553,069 A * | 11/1985 | Purser ...................... | 315/111.81 |
| 2002/0044626 A1 * | 4/2002 | Verman et al. .................. | 378/84 |
| 2003/0152194 A1 | 8/2003 | Nordmeyer et al. | |
| 2005/0220266 A1 * | 10/2005 | Hirsch ............................ | 378/43 |

OTHER PUBLICATIONS

Barron, R.F., "Cryogenic Heat Transfer," Taylor & Francis, 1999.
Ducohet, Jacques, et al., "Cryo-electron microscopy of vitrified specimens," Quarterly Reviews of Biophysics, 21:129-228, 1988.

(Continued)

*Primary Examiner* — Glen Kao
(74) *Attorney, Agent, or Firm* — Houston & Associates, LLP

(57) ABSTRACT

A cartridge-based cryogenic imaging system includes a sample handling system. This system uses a kinematic base and cold interface system that provides vertical loading to horizontally mounted high-precision rotation stages that are able to facilitate automated high-resolution three-dimensional (3D) imaging with computed tomography (CT). Flexible metal braids are used to provide cooling and also allow a large range of rotation. A robotic sample transfer and loading system provides further automation by allowing a number of samples to be loaded and automatically sequentially placed on the sample stage and imaged. These characteristics provide the capability of high-throughput and highly automated cryogenic x-ray microscopy and computed tomography.

16 Claims, 3 Drawing Sheets

(56) References Cited

OTHER PUBLICATIONS

Garman, E., "Cool data: quantity and quality," Acta Crystallographica D, 55:1641-1653, 1999.

Howells, M.R., "An assessment of the resolution limitation due to radiation-damage in X-ray diffraction microscopy," Journal of Electron Spectroscopy and Related Phenomena, in press:0, 2007. [Actually vol. 170, p. 4, 2009].

Iancu, Cristina V., et al., "A comparison of liquid nitrogen and liquid as cryogens for electron cryotomography" Journal of Structural Biology, 153(3):231-240, 2006.

Leapman, Richard D., et al, "Cryo-electron energy loss spectroscopy: observations on vitrified hydrated specimens and radiation damage," Ultramicroscopy, 59:71-79, 1995.

Maser, J., et al., "Soft x-ray microscopy with a cryo STXM: I. Instrumentation, imaging, and spectroscopy," Journal of Microscopy, 197(1):68-79, 2000.

Samson, Sten, et al., "A novel low-temperature x-ray goniometer with closed-cycle cooling to about 18 K," Journal of Applied Crystallography, 13:425-432, 1980.

Schneider, Gerd, "Cryo x-ray microscopy with high spatial resolution in amplitude and phase contrast," Ultramicroscopy, 75:85-104, 1998.

Schwartz, Cindi L., et al, "Cryo-fluorescence microscopy facilitates correlations between light and cryo-electron microscopy and reduces the rate of photobleaching," Journal of Microscopy, 227:98-109, 2007.

Shapiro, David, "Biological imaging by soft x-ray diffraction microscopy," PhD thesis, Department of Physics and Astronomy, Stony Brook University, 2004.

Steinbrecht, R., A, and K. Zierold, editors, "Cryotechniques in Biological Electron Microscopy," Berlin, 1987. Springer-Verlag.

Sun, S. Q., et al, "Quantitative water mapping of cryosectioned cells by electron energy-loss spectroscopy," Journal of Microscopy, 177(1):18-30, 1995.

Taylor, Kenneth A., et al., "Electron diffraction of frozen, hydrated protein crystals," Science, 106:1036-1037, 1974.

Taylor, Kenneth A., et al., Electron microscopy of frozen hydrated biological specimens. Journal of Ultrastructure Research, 55:448-456, 1976.

\* cited by examiner

X-RAY MICROSCOPE SYSTEM WITH CRYOGENIC HANDLING SYSTEM AND METHOD

RELATED APPLICATIONS

This application is a Continuation of U.S. application Ser. No. 12/559,183, filed on Sep. 14, 2009, which claims the benefit under 35 USC 119(e) of U.S. Provisional Application No. 61/096,502, filed on Sep. 12, 2008, both of which are incorporated herein by reference in its entirety.

BACKGROUND OF THE INVENTION

Microscopy has played an important role in science and technology. One area where light and electron microscopy techniques have been indispensable is biological sciences. Light microscopy has allowed observation at 200 nanometer (nm) scale resolution, while electron microscopy has demonstrated atomic scale resolution with thin-sectioned specimens. Recent developments in x-ray microscopy have allowed thick hydrated samples with tens of nanometer resolution.

For most effective observations, cells and biological tissues must be imaged in a hydrated state in order to have the highest fidelity representation of the living state. But when imaging hydrated organic specimens using ionizing radiation, radiation damage often limits the quality and resolution of the images that can be obtained. The solution is to work with hydrated specimens that have been rapidly frozen so as to minimize the formation of crystalline ice in the specimens.

Cryogenic specimen handling methods were first developed in electron microscopy in 1974 by K. Taylor and R. Glaeser, see Electron diffraction of frozen, hydrated protein crystals. Science, 106:1036-1037, 1974, and by the late 1980s there was a considerable knowledge base in place regarding rapid freezing and cryo electron microscopy. Cryomicroscopy is also expected to be important in trace element mapping in fluorescence microprobes, since specimen drying is likely to affect the distribution of the diffusible ions that can play such important physiological roles. Cryogenic methods have also found wide spread use in protein crystallography, where the usual practice involves a cryogenic gas stream directed onto a specimen to cool it within an atmospheric pressure, room temperature environment.

SUMMARY OF THE INVENTION

Aspects of the present invention concern cryogenic sample handling systems for high-resolution microscopy applications, such as x-ray, optical, and/or electron microscopy. By using a cartridge sample mount and robotic sample handling system, highly automated sample transfer and loading can be achieved. These are essential components of a high-throughput automated cryogenic microscopy that maintains the temperature of the specimen at between 80 and 170 degrees Kelvin, for example, or lower.

This system uses a kinematic mount and cold interface system that provide vertical loading to horizontally mounted high-precision rotation stages that are able to facilitate automated high-resolution three-dimensional (3D) imaging with computed tomography (CT), Flexible metal braids are used to provide cooling and also allow a large range of rotation. A robotic sample transfer and loading system provides further automation by allowing a number of samples to be loaded and automatically sequentially placed on the sample stage and imaged. These characteristics provide the capability of high-throughput and highly automated cryogenic x-ray microscopy and computed tomography.

In general, according to one aspect, the invention features a cryogenic imaging system, comprising a kinematic base that receives cartridges on a cryogenic base, with each cartridge carrying a specimen. The system further includes a positioning stage and a warm-cold interface between the positioning stage and the cryogenic base. A flexible thermal linkage is included between the cryogenic base and a refrigeration source to provide conductive cooling. A robotic loading and transfer system accepts one or more cartridges and load the cartridges onto the cryogenic base, and a microscopy system images specimens in the cartridges.

In one example, this microscopy system comprises an x-ray source for generating an x-ray beam that irradiates the cartridges on the cryogenic base and a detector for detecting the x-ray beam from the cartridges.

In embodiments, the positioning stage positions the cryogenic base along three axes and also rotates the cryogenic base. The warm-cold interface comprises a ball and groove configuration for low thermal conductivity. The flexible thermal linkage includes one or more metal wires.

In general, according to another aspect, the invention features, a cryogenic x-ray imaging method, comprising generating an x-ray beam that irradiates specimens, detecting the x-ray beam from the specimens, holding the specimens on a cryogenic base in the x-ray beam, positioning the specimens in the beam by moving the cryogenic base, and cooling the cryogenic base via a flexible thermal linkage between the cryogenic base and a refrigeration source.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The radiation biology literature uses the International System (Si) unit of the Gray (equal to one Joule of absorbed energy per kilogram of mass) as its unit of radiation dose. At 100 keV in transmission electron microscopes (TEM), an electron exposure of 1 $e^{-}/^2$ corresponds to a radiation dose of about $3 \times 10^4$ Gray, From both protein crystallography and electron microscopy or crystallography data, diffraction spots corresponding to atom resolution information begin to fade at radiation doses in the $10^7$-$10^8$ Gray range, with diffraction spots corresponding to 2-10 nm structural information fading at $10^8$-$10^9$ Gray.

In electron microscopy, radiation doses of about 1000 $e^-/nm^2$ or about $3\times10^7$ Gray lead to the onset of "bubbling" in the specimen, where water is broken down into $OH^-$ and $H^+$ and the hydrogen gas will form voids in the ice matrix when it is unable to diffuse through the ice; enhanced diffusion may explain the observation that in some cases liquid nitrogen temperatures are preferred to liquid helium temperatures.

In cryogenic x-ray microscopy, excellent structural preservation has been observed at radiation doses as high as $10^{10}$ Gray, without "bubbling". The absence of "bubbling" is presumably due to some combination of the lower dose rate relative to cryogenic electron microscopy (giving more time for diffusive release of H through the ice matrix) and the lower ratio of absorption in water versus organic materials at the 520 eV "water window" photon energies used in these experiments. These energies are just below the energy of the oxygen absorption edge. Sensitive coherence-based "speckle" measurements have shown that there is no measurable shrinkage of frozen hydrated cryo specimens, at least at doses up to $10^{10}$ Gray.

These studies emphasize the essential nature of cryogenic approaches for x-ray microscopy of hydrated organic specimens such as cells and tissues. For tomography, the specimen must remain constant as projections from different viewing angles are acquired so that all the individual views provide true representations of the object that is to be reconstructed. For spectrum imaging/spectromicroscopy image sequences, the specimen must not shrink or otherwise change its morphology so that all images can be registered to each other to yield a spectrum per pixel for subsequent analysis. For trace element mapping, it is important to not lose side groups that might be bound to the very elements one is hoping to measure and quantify. Cryogenics is essential to realize these important x-ray microscopy techniques.

Figure 1:
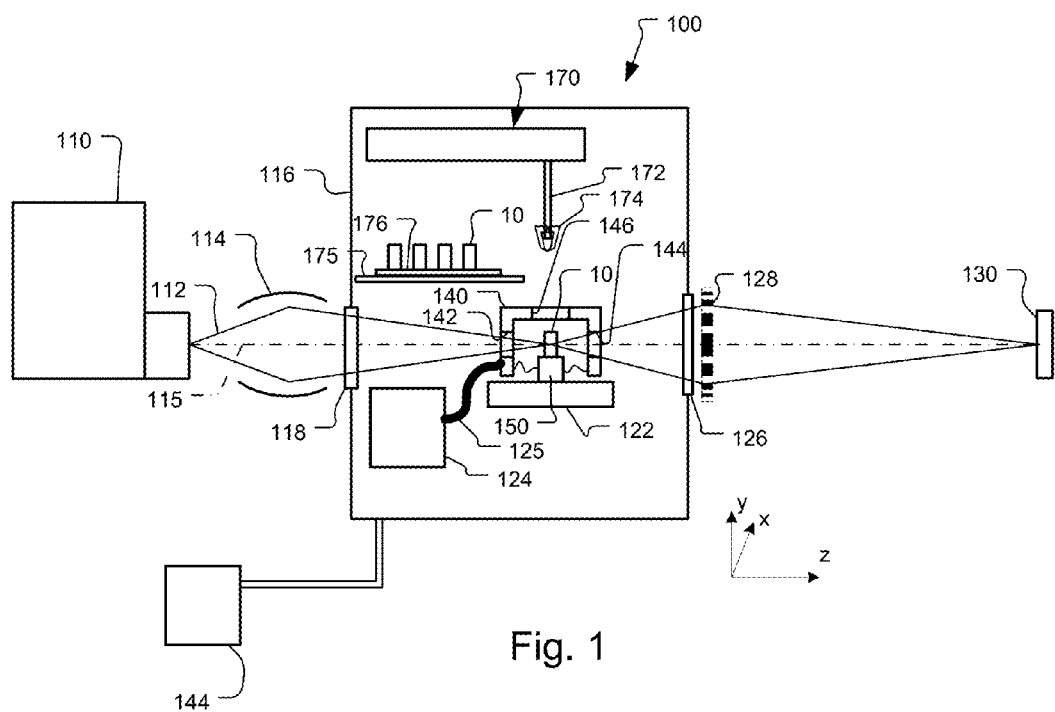
FIG. 1 is a schematic diagram of a cryogenic x-ray imaging system according to the present invention.

FIG. 1 shows a cyrogenic x-ray imaging system 100 that has been constructed according to the principles of the present invention.

In more detail, the system has an x-ray source 110 that generates an x-ray beam 112, In the one embodiment, the source 110 is a beamline of a synchrotron x-ray generation facility. In other embodiments, smaller sources are used, such as laboratory sources, For example, laboratory sources that generate x-rays by bonibarding a solid target anode with energetic electrons are one possible source that could be used, including microfocus and rotating anode type sources.

In still other embodiments, the imaging modality is other than x-rays, In one such embodiment, the source generates an electron beam or an optical beam.

The condenser 114 collects and focuses the x-ray beam 112 from the source 110. For the full field imaging setup, a suitable illumination of the sample 10 is required, This is most conveniently achieved by the use of a zone plate condenser, capillary, or Wolter optic.

When the imaging modality is an electron beam or an optical beam, other condenser systems are used such as focusing magnets or refractive/reflective optics, respectively.

A chamber or housing 116 is used to create a controlled environment for the specimens. The x-ray beam 112 enters the housing 116 through a housing input window 118. In some examples, the inside of the housing 116 is cooled to cryogenic temperatures such as less than 274 Kelvin (K) and usually about 77K, the temperature of liquid nitrogen, or colder. It is therefore insulated from the surrounding atmosphere. In other examples, the housing 116 is capable of holding a vacuum. In such cases, a vacuum pump system 144, such as a system including a turbomolecular pump, is in communication with the housing 116 via a pipe 152 in order to pull a vacuum within the housing 116.

The x-ray or other beam 112 is projected onto the specimen that is contained within a cartridge 10, The cartridge 10 is held on a horizontally extending base 150. This base 150 is a kinematic unit that positions the sample cartridge 10 along both the x, y, and z, axes. The kinematic base 150 further has the capability of rotating the specimen/cartridge 10 around the y axis to enable the acquisition of tomographic projections at different angles to the axis 115 of the x-ray beam 112.

The kinematic base 150 is held on a mounting plate 122. Then, on top of the kinematic base 150 and mounting plate 122, a cryogenic shield 140 surrounds the cartridge 10. This cryogenic shield 140 includes a shield input beam port 142 through which the beam 112 passes to the sample cartridge 10. A shield output beam port 144 of the cryogenic shield 140 allows the beam to exit after passing through the specimen/cartridge 10.

A refrigeration source 124 is preferably located within the housing 116. It is connected via a heat transfer element 125 to the cryogenic shield 140. In one example, this refrigeration source 124 is a refrigeration unit. In other examples, the refrigeration source 124 is a dewar or other container containing liquid nitrogen. The heat transfer element 125 is constructed from a high thermal transfer material such as braided copper cable.

The beam 112 from the sample cartridge 10 exits the cryogenic housing 116 through a housing output port 126. An x-ray objective 128 collects x-rays 112 from the specimen and images the x-ray beam 112 onto a detector system 130. In a current embodiment, the objective 128 is a Fresnel zone plate.

In examples where the beam 112 is an optical beam, the image is formed with refractive or reflective optics.

The detector system 130 is preferably a high-resolution, high-efficiency scintillator-coupled CCD (charge coupled device) camera system for detecting x-rays from the specimen. In one example, a camera system 130 as described in U.S. Pat. No. 7,057,187, which is incorporated herein by this reference in its entirety, is used.

A robotic loading and unloading system is provided in the preferred embodiment. Microscopy specimens are delicate and have a poor chance of surviving repeated handling. For this reason it is good practice to mount them once in a cartridge, and then handle that cartridge in subsequent operations. Cartridges 10 are loaded into the system 100 on a shuttle 176. A robot system 170 then individually loads and unloads the cartridges 10 onto kinematic base 150.

Cartridge covers are preferably used to prevent contamination buildup on the specimen during the various handling steps. Further the cartridges 10 preferably all share a common design in the top that is grabbed by the robot system's gripper 174 and for the end that is inserted into the kinematic base 150. Preferably, a unified base can support a variety of specimen mounting schemes. For example, one type of cartridge might use clamping rings for standard 3 mm TEM grids, another might use a micro-fabricated silicon stalk to minimize x-ray fluorescence background while maintaining good dimensional stability and thermal conductivity, while yet another might use a thin-walled capillary for the mounting of tomography specimens.

A horizontal linear travel stage 175 is used to move the shuttle base 176 from a position well out of the way of the kinematic base 150, to a series of locations that put each of the cartridges 10 or cartridges slots in the shuttle 176 directly above the center of the kinematic base 150 and the loading port 146 formed in the cryo shield 140. A robot arm 172 the picks the cartridges with the gripper 174 and transfers the cartridges 10 between the kinematic base 150 and the cartridge slots of the shuttle 176, accessing the kinematic base 150 via the loading port 146.

The robot system 170 preferably has a vertical linear travel stage 172 upon which the gripper 174 is mounted. A fiberglass insert provides thermal isolation for the gripper end 174 which is in turn conductively cooled using a copper braid to a dewar, in one example. This requires access to the specimen from above, and either enough "headroom" in the chamber 116 to hold the vertical linear travel stage upon which the robot grabber is mounted, or a port with a linear feedthrough.

Figure 2:
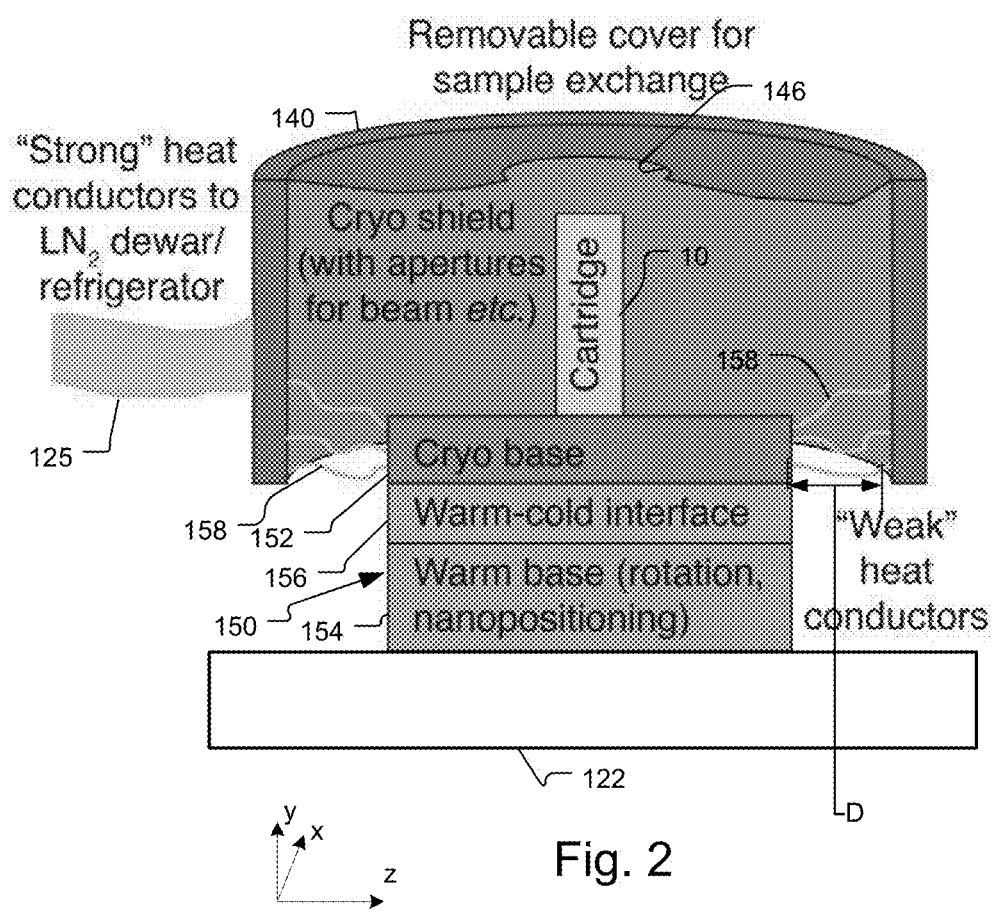
FIG. 2 is a schematic diagram of a kinematic base 150 and cryogenic shield according to the present invention.

FIG. 2 shows the details of the kinematic base 150 and shield 140.

A small, low-mass cryo base 152 is mounted on a high-temperature rotation and/or nanopositioning stage 1154 that is supported on the mounting plate 122. The nanopositioning stage 1154 positions and moves the cryo base 152 and thus the specimen in the cartridge 10 along the x, y and z axes to position the region of interest of the specimen within the x-ray beam 115, and also preferably rotates the specimen about the y axis.

A warm-cold interface 156 separates the nanopositioning stage 154 from the cryo base 152. It is constructed from an interface material and has a geometry with tow mechanical creep and low thermal conductance.

The cold cryo base 152 mainly "sees" the area of the cryo shield 140, radiative heat transfer into the specimen 110 is thus greatly reduced. The dominant heat transfer path becomes that of the warm-cold interface 156, which has both high mechanical stiffness and low thermal conductivity. In this way only modest cooling power (well below 100 milli-Watts (mW)) must be supplied to the cryo base 152. This is preferably supplied by "weak" heat conductors 158 which involve very low mechanical coupling force between the cryo base 152 and the cryo shield 140 for rotations up to ±90 of the cryo base by the movement of the nanopositioning stage 154 or translations of several millimeters. (Initial cool-down involves moving a raised surface on the cryo base into strong contact with a cold "finger" from the cryo shield). This cryo base 152 is normally kept cold in the microscope 1100 at all times.

Key thermal design considerations for this approach include the following: Gas conductivity becomes negligible at pressures of below about $10^{-4}$ torr, and pressures well below this are needed to minimize ice buildup on cryo specimens. Because the thermal conductivity of high-purity copper increases at lower temperatures, weak heat conductors 158 comprise a number of copper wires that can provide good thermal cooling power, such as less than 500 wires. As an example, 150 wires in parallel, each 100 micrometers ($\mu$m) in diameter and 50 millimeters (mm) long, can provide 120 mW of cooling power over a temperature difference of 10 K between the cryo shield 140 that is cooled by the heat conduction through heat transfer element 125 to the refrigeration source 124. The wire conductors 158 are much longer than the distance (D) between the outer wall of the base 152 and the shield 140 so that the base 1152 is moved and rotated freely by the nanopositioning stage 154. In one example, the length of the wire conductors 158 are more than 5 times distance D.

Figure 3:
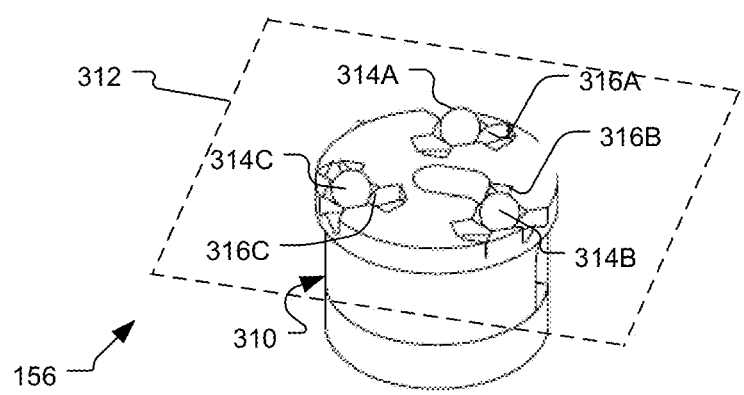
FIG. 3 is a scale drawing of a warm-cold interface of the kinematic base according to the present invention.

FIG. 3 shows an embodiment of the warm-cold interface 156.

In more detail, the warm-cold interface 156 comprises an upper member 312 on which the cryogenic base 152 is placed and lower member 310 that is secured to the nanopositioning stage 154.

Both the upper member 312 and lower member 310 have low emissivity coatings, especially on the two surfaces that face each other. For example, using a conservative estimate for the emissivity ($\epsilon$) of highly polished gold of $\epsilon=0.05$ (as opposed to the $\epsilon=0.018$-$0.035$ values given in published tables), the radiative heat transfer between two 25 mm disks when one is at 100 K and the other at 300 K is only about 11 mW. Thermal conductivity then becomes the dominant path. This is controlled by using a ball-on-flat mounting approach and with both low conductivity materials. Preferably, both the upper member 312 and lower member 310 are constructed from fused silica or an infrared glass. AMTIR-1, from Amorphous Materials Inc, for example, has 5× lower conductivity and nearly equal stiffness.

The current ball-on flat approach to thermal isolation uses three recesses 316A, 316B, 316C are formed in the lower member 310. In the preferred embodiment, each of these three recesses 316A, 316B, 316C comprises three planar surfaces in the general form of a pyramid. In an alternative design, the three recesses 316A, 316B, 316C are in the form of a cone. Low thermal conductivity balls or spheres 314A, 314B, 314C are each placed in a corresponding one of the three recesses 316A, 316B, 316C. The upper member 312 has a corresponding, mirrored series of recesses that receive the balls 314A, 314B, 314C. This creates rigid yet low thermal conductivity interface.

Depending on the choice of materials and the force applied, a thermal conduction power of no more than 20-50 mW can be obtained between the cryo base 152 and the warm nanopositioning stage 154. This ball-oh-fiat system implemented in the upper member, 312, tower member 310 and balls or spheres 314A, 314B, 314C also has the advantage of being naturally suited to a kinematic mounting system, where no mechanical stress is induced that would otherwise lead to mechanical drift. Other design configurations can include the commonly used ball-groove-flat kinematic mounting system.

While this invention has been particularly shown and described with references to preferred embodiments thereof, it will be understood by those skilled in the art that various changes in form and details may be made therein without departing from the scope of the invention encompassed by the appended claims.

What is claimed is:

1. A cryogenic x-ray imaging method, comprising:
    generating an x-ray beam that irradiates specimens;
    detecting the x-ray beam from the specimens;
    holding the specimens on a cryogenic base in the x-ray beam in a vacuum chamber;
    positioning the specimens in the beam by rotating the cryogenic base using a positioning stage that is located entirely within the vacuum chamber;
    cooling the cryogenic base via a flexible thermal linkage between the cryogenic base and a refrigeration source; and
    positioning a region of interest of the specimen on the cryogenic base in the beam by moving the cryogenic base along two or more axes using the positioning stage.

2. A method as claimed in claim 1, further comprising robotically loading and unloading specimens from the cryogenic base.

3. A method as claimed in claim 1, further comprising positioning the cryogenic base along three axes.

4. A method as claimed in claim 1, further comprising providing a low thermal conductivity mechanical interface between the cryogenic base and the positioning stage.

5. A method as claimed in claim 1, further comprising thermally shielding the cryogenic base.

6. A method as claimed in claim 1, further comprising connecting the flexible thermal linkage between the cryogenic base and a cryogenic shield for the cryogenic base.

7. A method as claimed in claim 1, further comprising rotating the specimens by the rotation of the cryogenic base with the positioning stage and acquiring tomographic projections at different angles.

8. A method as claimed in claim 1, further comprising collecting and focusing the x-ray beam from a source onto the specimens.

9. A method as claimed in claim 1, further comprising using a laboratory x-ray source to generate the x-ray beam.

10. A method as claimed in claim 1, further comprising robotically loading and unloading specimens from the cryogenic base with a robot system located within the vacuum chamber with the specimens.

11. A cryogenic x-ray imaging method, comprising:
generating an x-ray beam that irradiates specimens;
detecting the x-ray beam from the specimens;
holding the specimens on a cryogenic base in the x-ray beam in a vacuum chamber;
positioning the specimens in the beam by rotating the cryogenic base using a positioning stage that is located within the vacuum chamber;
cooling the cryogenic base via a flexible thermal linkage between the cryogenic base and a stationary cryogenic shield, which is thermally connected to a refrigeration source; and
robotically loading and unloading specimens from the cryogenic base through a loading port formed in the cryogenic shield with a robot system located within the vacuum chamber.

12. A method as claimed in claim 11, further comprising positioning the cryogenic base along three axes in the x-ray beam with the positioning stage.

13. A method as claimed in claim 11, further comprising providing a low thermal conductivity mechanical interface between the cryogenic base and the positioning stage.

14. A method as claimed in claim 11, further comprising rotating the specimens and acquiring tomographic projections at different angles.

15. A method as claimed in claim 11, further comprising using a laboratory x-ray source to generate the x-ray beam.

16. A method as claimed in claim 11, further comprising positioning a region of interest of the specimens on the cryogenic base in the beam by moving the cryogenic base along two or more axes using the positioning stage.

* * * * *